United States Patent [19]

Kawasaki et al.

[11] Patent Number: 5,223,641
[45] Date of Patent: Jun. 29, 1993

[54] CARBOXYLIC ACID MIXTURES AND PROCESS FOR PRODUCING THE SAME

[75] Inventors: Hiroshi Kawasaki, Yamaguchi; Hideaki Miwa, Tokyo; Osamu Ichihara, Yamaguchi, all of Japan

[73] Assignee: Idemitsu Petrochemical Chemical Company, Limited, Tokyo, Japan

[21] Appl. No.: 915,386

[22] Filed: Jul. 20, 1992

Related U.S. Application Data

[63] Continuation of Ser. No. 595,734, Oct. 9, 1990, abandoned, which is a continuation-in-part of Ser. No. 358,021, May 30, 1989, abandoned, which is a continuation-in-part of Ser. No. 72,498, Jul. 13, 1987, abandoned.

[30] Foreign Application Priority Data

Jan. 14, 1986 [JP] Japan .................................. 61-5748
Jun. 23, 1987 [JP] Japan .............................. 62-156089
Jun. 30, 1987 [JP] Japan .............................. 61-165057

[51] Int. Cl.$^5$ .......................................... C07C 51/14
[52] U.S. Cl. ...................................................... 562/521
[58] Field of Search ........................................ 562/521

[56] References Cited

U.S. PATENT DOCUMENTS 3,910,963 10/1975 Souma et al. ............... 260/413 X
4,002,577 1/1977 Koyano et al. ............. 260/413 X

FOREIGN PATENT DOCUMENTS 1016087 1/1966 United Kingdom .

OTHER PUBLICATIONS

Chem Abs., vol. 89, No. 13, Sep. 25, 1978, p. 789, abstract No. 108019q. Columbus, Ohio, US Y. Souma et al.: "Carbonylation of olefin and alcohol catalyzed by copper (I) carbonyl in hydrogen fluoride" & Osaka Kogyo Gijutsu Shikensho Kiho, 1978, 29 (2), 106-9.
Patent Abstracts of Japan; vol. 12, No. 5, (C-467)(2852), Jan. 8, 1988, & JP-A-62 164 645 (Idemitsu Petro--Chem. Co. Ltd.) Jul. 21, 1987.
Patent Abstracts of Japan; vol. 12, No. 47 (C-475) (2894), Feb. 12, 1988 & JP-A-62-192 338 (Idemitsu Petro-Chem. Co. Ltd.) Aug. 22, 1987.

*Primary Examiner*—José G. Dees
*Assistant Examiner*—Joseph M. Conrad, III
*Attorney, Agent, or Firm*—Browdy and Neimark

[57] ABSTRACT

Disclosed is a process for the production of carboxylic acids providing esters unlikely to be hydrolyzable, which comprises reacting a polyolefin containing an isobutylene unit at a rate of 60% by weight or higher with monoxide and water in the presence of a catalyst in an amount of sulfuric acid in the catalyst of 3 moles or more with respect to mole of C═C double bonds in the polyolefin and in amounts of carbon monoxide and water of at least a mole equivalent to the C═C double bonds in the polyolefin, said catalyst being a catalyst comprising a sulfuric acid aqueous solution in concentrations of 73% to 98% by weight and a catalyst comprising a sulfuric acid aqueous solution in concentrations of 73% to 98% by weight and phosphoric acid, each having an acid strength within a range from −6 to −9.2 or said catalyst comprising a sulfuric acid aqueous solution in concentrations of 73% to 98% by weight, phosphoric acid in concentrations of 70% by weight or less with respect to the combined quantity of the sulfuric acid aqueous solution and phosphoric acid, and a metal oxide in concentrations of 0.1% to 4% by weight with respect to the combined quantity of the sulfuric acid aqueous solution and phosphoric acid.

10 Claims, No Drawings

CARBOXYLIC ACID MIXTURES AND PROCESS FOR PRODUCING THE SAME

This application is a continuation, of application Ser. No. 07/595,734, filed Oct. 9, 1990, now abandoned which is a continuation-in-part of U.S. Ser. No. 07/358,021, filed May 30, 1989, now abandoned which is a continuation-in-part of U.S. Ser. No. 07/072,498, filed Jul. 13, 1987, now abandoned.

BACKGROUND OF THE INVENTION

1. Field of the Invention

The present invention relates to a process for the production of carboxylic acids and, more particularly, to a process for the production of carboxylic acids which are less in content of impurities such as sulfur compounds and unlikely to be esterifiable.

2. Description of Related Art

Esters of tertiary carboxylic acids are widely used as ingredient for coating compositions, solvents, and the like. Esters of tertiary carboxylic acids to be used therefor are required to be high in a resistance to hydrolysis because they are exposed to severe conditions for a long period of time.

It is known that the carboxylic acid mixture mainly composed of the tertiary carboxylic acids used for the production of tertiary acid esters for the above uses is prepared by a so-called Koch's reaction.

This Koch's reaction involves reacting an olefin or an alcohol with carbon monoxide and water in the presence of an acid catalyst containing hydrochloric acid, sulfuric acid, phosphoric acid or boron trifluoride to produce a carboxylic acid having carbon atoms more than the olefin or alcohol used as a starting material by one carbon atom.

Processes for the production of tertiary carboxylic acids include the following various processes.

For example, Japanese Patent Unexamined Publication (laid-open) No. 35,048/73 has proposed a process for the production of a branched-chain carboxylic acid which is characterized in that prior to distillation of a crude fatty acid obtained by removing sulfuric acid catalyst from a reaction product, or a so-called Koch's reaction product, obtained by the reaction of an olefin with carbon monoxide and water in the presence of the sulfuric acid catalyst, the crude fatty acid is heated in a liquid phase at 100° to 270° C. together with water or water containing a small amount of an organic or inorganic acid salt.

This patent publication discloses, as examples of sulfuric acid catalysts, an aqueous sulfuric acid solution of more than about 80% by weight in concentration or concentrated sulfuric acid or mixtures of these sulfuric acids with at least one of boron trifluoride, hydrogen fluoride and phosphoric acid. However, as shown in Example 1, the process is carried out under high pressure condition of as high as 70 kg/cm$^2$ in carbon monoxide pressure. Besides, this process gives only crude fatty acid mixtures containing 41.8% by weight of trichloroethylene, 42.3% by weight of branched C9 carboxylic acids and 6.2% by weight of C13 carboxylic acids. As a result of purification of such crude fatty acid mixtures, there was produced merely a C9 carboxylic acid mixture containing 49.4% by weight of 2,2,4,4-tetramethylpentanoic acid and 44.4% by weight of a mixture of 2,3,3-trimethyl-2-ethylbutanoic acid, 2,2-diisopropylpropanoic acid, 2,2,3,4-tetramethylpentanoic acid and 2,2,3,3-tetramethylpentanoic acid. Thus, a mixture of such tertiary carboxylic acids producing an ester unlikely to be hydrolyzable was obtained at the rate of as low as 50% or less. The similar result was obtained in Example 2.

On the other hand, Japanese Patent Examined Publication No. 3,362/55 discloses a process for the production of a carboxylic acid from an olefin and carbon monoxide in the presence of a catalyst including at least 90% sulfuric acid or anhydrous hydrogen fluoride alone or mixed with boron fluoride, which is characterized in that the reaction is first carried out in a liquid phase without adding water and then the reaction product was taken in water and treated at room temperature. This patent publication discloses, in Example 4, an example of the production of carboxylic acids mainly composed of trimethylacetic acid by introducing isobutene into an autoclave containing carbon monoxide kept at 50 atm. in the presence of 97% sulfuric acid and carrying out reaction at 6° to 10° C. for 4.5 hours. In other examples of the prior patent publication, there were also produced carboxylic acids which provide esters which are easily hydrolyzed. Thus, this patent publication discloses a process for the production of easily hydrolyzable carboxylic acids and does not disclose those which provide esters which cannot be easily hydrolyzed as in this invention.

Further, Japanese Patent Unexamined Publication No. 48,619/74 discloses a process for the production of a tertiary carboxylic acid which comprises subjecting an alcohol or olefin of at least 4 carbon atoms to addition reaction of carbon monoxide in the presence of copper, silver or gold alone or a mixed monovalent compound (excluding halides, cyanides and nitrate) using at least 80% sulfuric acid, hydrogen fluoride, fluorosulfuric acid, phosphoric acid or boron fluoride complex as a solvent under a carbon monoxide partial pressure of 0.1 atm. or higher and at −10° C. to 70° C.

However, Example 2 of this patent publication discloses an example of production of a mixture of 2,2-dimethylnonanoic acid and 2-methyl-2-ethyloctanoic acid from heptene-1 in a ratio of the former to the latter of 3 to 2 using 100% sulfuric acid as a solvent and cuprous oxide and aurous oxide as catalyst; Example 4 shows an example of production of pivalic acid from butene-1 in the yield of about 40% based on the olefin used using 88% sulfuric acid as a solvent and cuprous oxide and silver oxide as catalyst; and Example 6 shows an example of production of a 3:1 mixture of 2,2-dimethylheptanoic acid and 2-methyl-2-ethylhexanoic acid from 2-ethylhexene-1 using phosphoric acid as a solvent and a complex of boron fluoride with acetic acid and cuprous oxide as catalyst. It is to be noted, however, that all of these examples merely show the production of tertiary carboxylic acids which provide esters easily hydrolyzable.

Norihiko Yoneda et al., "Chemistry Letters", 1984, pp. 607–610 discloses carbonylation reaction of diisobutylene with carbon monoxide in BF$_3$-H$_2$O using Cu(I) carbonyl as a catalyst. According to this process for the production of carboxylic acids from diisobutylene shown in the above literature, the reaction without using a solvent gives carboxylic acids in a yield of 77% which comprises 32% of 32% of C5 carboxylic acids, 13% of C6-8 carboxylic acids, 36% of C9 carboxylic acids, and 19% of other carboxylic acids, while the reaction using a solvent such as cyclohexane or chlorobenzene produces carboxylic acids in yields of 80% to 82%, which comprises 41-44% of C5 carboxylic acids, 11-14% of C6-8 carboxylic acids, 35-36% of C9 carboxylic acids, and 9-10% of other carboxylic acids. Thus, the process disclosed in this literature is low in yields of carboxylic acids and besides produces only the products mainly composed of carboxylic acids which provide easily hydrolyzable esters.

Yoshie Souma et al., "Oil Chemistry", vol. 30, No. 5, p. 265 and Yoshie Souma, "Organic Synthetic Chemistry", vol. 41, p. 561-569, 1983, also disclose synthesis of carboxylic acids from olefins with metallic carbonyl catalysts, but the synthesis produces carboxylic acids in low yields and can provide only products mainly composed of such carboxylic acids so providing esters which are easily hydrolyzed.

Japanese Patent Examined Publication No. 16,897/73 discloses a purification process which is characterized by contacting an oxidizing agent with a crude fatty acid obtained by removing sulfuric acid catalyst from a so-called Koch's reaction product obtained by reacting an olefin with carbon monoxide and water in the presence of sulfuric acid catalyst prior to distillation of the crude fatty acid.

SUMMARY OF THE INVENTION

An object of the present invention is to provide a process for producing carboxylic acids which provide an ester unlikely to be readily hydrolyzable.

The present invention provides a process capable of reusing the used catalyst in a repeated manner in the step of manufacturing carboxylic acids by means of the Koch's reaction and, furthermore, capable of producing a carboxylic acid containing a lesser amount of sulfur compounds as impurities even if the catalyst is repeatedly used.

Furthermore, the present invention has another object to provide a process for the production of a carboxylic acid with higher selectivity, which has carbon atoms by one carbon atom more than the polyolefin used as the starting material in which the isobutylene unit is contained at the rate of 60% by weight or higher.

In order to achieve the above objects, the present invention consists of a process for the production of carboxylic acids providing esters unlikely to be hydrolyzable, which comprises reacting a polyolefin containing an isobutylene unit at a rate of 60% by weight or higher with monoxide and water under reaction pressure ranging from 2 to 40 kg/cm$^2$ at reaction temperature ranging from $-10°$ C. to 80° C. in the presence of a catalyst in an amount of sulfuric acid in the catalyst of 3 moles or more with respect to mole of C=C double bonds in the polyolefin and in amounts of carbon monoxide and water of at least a mole equivalent to the C=C double bonds in the polyolefin, said catalyst being selected from the group consisting of a catalyst comprising a sulfuric acid aqueous solution in concentrations of 73% to 98% by weight and a catalyst comprising a sulfuric acid aqueous solution in concentrations of 73% to 98% by weight and phosphoric acid, each having an acid strength within a range from $-6$ to $-9.2$ or said catalyst comprising a sulfuric acid aqueous solution in concentrations of 73% to 98% by weight, phosphoric acid in concentrations of 70% by weight or less with respect to the combined quantity of the sulfuric acid aqueous solution and phosphoric acid, and a metal oxide in concentrations of 0.1% to 4% by weight with respect to the combined quantity of the sulfuric acid aqueous solution and phosphoric acid.

DESCRIPTION OF THE PREFERRED EMBODIMENTS

The term "unlikely to be esterifiable" and related terms used herein may be defined as follows:

A carboxylic acid is defined in this specification as being unlikely to be esterifiable when a conversion rate of the resulting carboxylic acid to the corresponding ester of 40% or less as a result of analysis by gas chromatography under the following analytical conditions. The analysis is carried out using the reaction product obtained when a carboxylic acid is reacted with methanol in an amount of 4 times the weight of the carboxylic acid in the presence of zinc acetate as a catalyst in an amount of 5.4% by weight of the carboxylic acid at a reaction temperature of 200° C. for a reaction time of 5 hours.

Analytical conditions

Gas chromatography device: Type GC-9A (Shimadzu Seisakusho K.K.)

Column packing material: FON (Trade name for product of Shimadzu Seisakusho K.K.)

Column diameter: $3\phi \times 2$ m

Column temperature: Elevated from 100° C. to 250° C.

Temperature elevation rate: 10° C. per minute

Detector: FID

Injection: 250° C.

It can be presumed that tertiary carboxylic acids with their carboxyl groups surrounded by bulky groups are unlikely to be esterified under the above esterification conditions due to the steric hindrance. It is thus to be noted that the tertiary carboxylic acids suffering steric hindrance can provide such characteristic that when they are esterified under esterification conditions severer than the above esterification conditions, the resulting esters do not easily undergo hydrolysis. In other words, esters of such tertiary carboxylic acids as suffering steric hindrance have a resistance to hydrolysis.

The term "resistance to hydrolysis" and related terms can be defined as follows:

A carboxylic acid may be defined as having "a resistance to hydrolysis", or as being "unlikely to be hydrolyzable" when a conversion rate of the carboxylic acid ester to the carboxylic acid of 40% or lower as a result of analysis by gas chromatography under the following analytical conditions. The analysis is carried out by subjecting methyl ester of the corresponding carboxylic acid in a 0.1 N sodium hydroxide solution (a mixture of water with ethylene glycol monomethyl ether at the ratio of the former to the latter of 1 to 10) to alkali hydrolysis while leaving the mixture to stand in a thermostatic chamber at 80° C. for 50 hours to carry out alkali hydrolysis.

Analytical conditions

Gas chromatography device: Type GC-9A (Shimadzu Seisakusho K.K.)

Column packing material: FON (Trade name for product of Shimadzu Seisakusho K.K.)

Column diameter: $3\phi \times 2$ m

Column temperature: Elevated from 100° C. to 250° C.

Temperature elevation rate: 10° C. per minute

Detector: FID

Injection: 250° C.

Therefore, the carboxylic acids of the present invention, when esterified, are useful as chemically stable coating compositions and solvents.

The carboxylic acid unlikely to be esterifiable may be produced by the process of the present invention.

A starting material to be used for the process according to the present invention may be a polyolefin containing an isobutylene unit at the rate of 60% by weight. It should be understood that the term "polyolefin" referred to herein is intended to mean one containing the isobutylene unit at the rate of 60% by weight or higher so that it may include a mixture of polyolefins and one which comprises a single polyolefin. As long as the amount of the isobutylene unit is satisfied, the polyolefin may contain a substance such as a paraffin in an amount which does not impair the object of the present invention. The polyolefin may include a polyolefin mixture containing 60% by weight or higher, preferably from 71% to 74% by weight, of the isobutylene unit, which is obtainable by polymerization of a butane-butylene fraction from the craking of naphtha in the presence of a Lewis catalyst such as aluminum chloride catalyst or a polyolefin mixture containing an isobutylene oligomer such as diisobutylene, triisobutylene or the like together with the isobutylene unit at the rate of 60% by weight or more.

Carbon monoxide used in the process according to the present invention is most preferably pure carbon monoxide, but carbon monoxide-containing gases obtained from water gas, generator gas, coke oven gas, and the like, may also be used.

Water used in the process according to the present invention is most preferably pure water, but there may also be used distilled water, deionized water, and the like.

The catalyst to be used in the process according to the present invention may be a member selected from the group consisting of a catalyst comprising a sulfuric acid aqueous solution in concentrations of 73% to 98% by weight, each having an acid strength within a range from $-6$ to $-9.2$; a catalyst comprising a sulfuric acid aqueous solution in concentrations of 73% to 98% by weight and phosphoric acid, each having an acid strength within a range from $-6$ to $-9.2$; and said catalyst comprising a sulfuric acid aqueous solution in concentrations of 73% to 98% by weight, phosphoric acid in concentrations of 70% by weight or less with respect to the combined quantity of the sulfuric acid aqueous solution and phosphoric acid, and a metal oxide in concentrations of 0.1% to 4% by weight with respect to the combined quantity of the sulfuric acid aqueous solution and phosphoric acid.

The metal oxide includes cuprous oxide and silver oxide and cuprous oxide is more preferred.

The acid strength of the catalyst is within the range of $-9.2$ to $-6$, preferably $-9.0$ to $-6.5$.

The acid strength used herein means a Hammett's acidity function Ho. The Hammett's acidity function Ho is defined as a quantitative measure of a solvent's ability of providing a proton to a base and may be determined from color identification testing using an indicator A with a known pKa value on the basis of the following formula:

$$Ho = pKa + \log[A]/[AH]$$

where

[A] is a concentration of the indicator A; and

[AH] is a concentration of the indicator converted into a proton.

As the indicator A may be used anthraquinone.

When an acid strength of the catalyst used is higher than $-6$, on the one hand, carbonylation reaction is difficult to take place while polymerization or isomerization of olefins tends to occur. When it is lower than $-9.2$, on the other hand, carbonylation of an isobutylene oligomer used as an olefin is apt to occur while keeping its skeleton and furthermore, cleavage of an isobutylene monomer vigorously occurs to increase the tendency of the production of pivalic acid as a C5 acids in a greater amount.

Concentrations of sulfuric acid in the catalyst are in the range usually from 30% to 90% by weight, preferably from 40% to 80% by weight.

In this mixture of sulfuric acid and phosphoric acid there may be present water which is contained in sulfuric acid and phosphoric acid or added separately. A content of this water is usually not more than 25% by weight.

It is to be noted that no limitations are particularly placed on the method of preparation of catalysts. For example, a catalyst solution containing a mixture of sulfuric acid with phosphoric acid prepared by ordinary mixing procedures may be previously prepared and it may be used upon practical application as it is or as it is diluted.

Furthermore, a catalyst solution obtained by admixing the metal oxide with sulfuric acid and phosphoric acid may be prepared and then used as a catalyst.

Preferably, the starting materials are added to a reaction vessel where the catalyst components have previously been charged.

When cuprous oxide or silver oxide is used as one component of the catalyst, particularly when cuprous oxide is used, an amount of the metal oxide is normally in the range from 0.1% to 4% by weight, preferably 0.2-2% by weight, of the total weight of sulfuric acid and phosphoric acid to be used as components of the catalyst.

If the amount of the metal oxide is less than 0.1% by weight, there is the tendency of an increase in the production of hydrocarbon oil. If it is more than 4% by weight, a reaction result is not improved so much and rather an acid strength of the catalyst tends to increase leading to a decrease in a carbonylation activity as a result of formation of water.

An amount of the catalyst used may be such that an amount of sulfuric acid amounts to 3 moles or higher with respect to mole of C=C double bonds in the polyolefin.

In the process of the present invention, reaction pressure (gauge pressure) is in the range from 2 to 40 $kg/cm^2$, preferably from 4 to 20 $kg/cm^2$.

When the polyolefin containing diisobutylene used as starting material under the reaction pressure of higher than 40 $kg/cm^2$, there are produced larger amounts of carboxylic acids which provide esters poor in a resistance to hydrolysis, e.g., 2,2,4,4-tetramethylpentanoic acid. This is considered to occur because, under relatively high pressure conditions as exceeding 40 $kg/cm^2$, the isobutylene is converted to 2,2,4,4-tetramethylpentanoic acid while maintaining its skeleton, while under relatively low pressures as high as 2 to 40 $kg/cm^2$, the carbon skeleton of the diisobutylene converted through a repetition of a series of isomerization to a carboxylic acid which is chemically stable, in other words, more inert, e.g., 2-isopropyl-2,3-dimethylbutanoic acid, than 2,2,4,4-tetramethylpentanoic acid. If the reaction pressure is lower than 2 kg/cm$^2$, polymerization of only olefins takes place yet the reaction may not proceed to a sufficient extent.

Reaction temperatures may be conveniently selected from the range from $-10°$ C. to $80°$ C. and generally from $0°$ C. to $50°$ C. If the reaction temperature is lower than $0°$ C., a reaction velocity may decrease. If it is higher than $50°$ C., the formation of sulfuric acid sludge, sulfuric acid esters and the like may increase.

Reaction time is enough to ensure 45 to 120 minutes for feeding the polyolefin and 30 to 120 minutes for stirring.

The reaction of the polyolefin with carbon monoxide and water in the presence of the catalyst may be carried out by any procedures of any type such as batch, semi-batch, and continuous type.

After completion of the reaction, a carboxylic acid unlikely to be esterifiable can be obtained by separation and purification operation including, for example, extraction of the resulting reaction mixture with an organic solvent such as n-hexane, washing with water, removal of the solvent, and so on, thereby leading to formation of the carboxylic acid which is hard to esterify.

The process according to the present invention provides a carboxylic acid less esterifiable as the object of the present invention using a catalyst consisting merely of an aqueous sulfuric acid solution if the acid strength and reaction pressure are to be adjusted within given values. If there is used a catalyst containing sulfuric acid, phosphoric acid and, if required, the metal oxide selected from cuprous oxide and silver oxide, the resulting reaction product contains a less amount of sulfur compounds originating from the sulfuric acid that is one of the catalyst components and hence it is contaminated with such sulfur compounds in a lesser amount, resulting in the formation of a carboxylic acid free from coloration and malodor. Reasons why the use of the catalyst having the above composition can restrain the formation of the sulfur compound, however, are not clear.

However, even without theoretical elucidation for the mechanism of restraint of the production of sulfur compounds, the process according to the present invention is industrially advantageous for the production of carboxylic acids because it can produce carboxylic acids free from malodor and coloration in high yields while restraining formation of sulfur compounds.

The process according to the present invention provides a stable carboxylic acid producing an ester hardly hydrolyzable, which involves reacting the polyolefin containing the isobutylene unit at the rate of 60% by weight or higher as starting material in the presence of the catalyst selected from the group consisting of a catalyst comprising a sulfuric acid aqueous solution in concentrations of 73% to 98% by weight; a catalyst comprising a sulfuric acid aqueous solution in concentrations of 73% to 98% by weight and phosphoric acid, each having an acid strength within a range from $-6$ to $-9.2$; and a catalyst comprising a sulfuric acid aqueous solution in concentrations of 73% to 98% by weight, phosphoric acid in concentrations of 70% by weight or less with respect to the combined quantity of the sulfuric acid aqueous solution and phosphoric acid, and a metal oxide in concentrations of 0.1% to 4% by weight with respect to the combined quantity of the sulfuric acid aqueous solution and phosphoric acid, under the reaction pressure ranging from 2 to 40 kg/cm$^2$ at the reaction temperature ranging from $-10°$ C. to $80°$ C.

In the process according to the present invention, it is possible to recover a catalyst solution from the extracting solvent and reuse it by recirculation through the reaction system. The present invention presents the advantage in this respect, too. It is to be noted that, if the metal oxide including cuprous oxide or silver oxide is used as one of the catalyst components, the recovery of the catalyst solution is preferably carried out under ambient atmosphere in which the metal oxide is not oxidizable. The recovery of the catalyst solution under oxidative atmosphere may decrease a catalyst activity upon oxidation of the metal oxide, thus leading to a decrease in a yield of the carboxylic acid when the recovered catalyst is reused.

The process according to the present invention provides the following advantages:

(1) It is possible to selectively produce a carboxylic acid mixture containing at least 55% by weight of carboxylic acids which provide esters having a hydrolysis resistance.

(2) It is industrially advantageous because the reaction can be carried out at reaction pressures as low as from 2 to 40 kg/cm$^2$.

(3) The process of the present invention is an economical one because the catalyst used in the production can be recovered and reused.

The present invention will be described by way of examples with reference to comparative examples.

EXAMPLE 1

A one-liter magnetic stirring type stainless steel autoclave was charged with 270 g of a strong acid mixture composed of 64% by weight of sulfuric acid, 29% by weight of phosphoric acid and 7% by weight of water as well as 6.4 g of cuprous oxide and the inside of the autoclave was sufficiently purged with carbon monoxide gas. Then the mixture was stirred at 1,000 rpm for 3 hours at a temperature of $25°$ C. and a carbon monoxide pressure of 15 kg/cm$^3$ to thoroughly dissolve the cuprous oxide.

To this autoclave was fed 33.6 g (0.3 mole) of a diisobutylene mixture over a period of 90 minutes while keeping the same temperature and pressure. The diisobutylene mixture used was composed of 70.9% by weight of 2,4,4-trimethyl-1-pentene, 22.1% by weight of 2,4,4-trimethyl-2-pentene, and 7.0% by weight of other olefins having 8 carbons. Carbon monoxide consumed during the reaction was replenished to the autoclave so as to keep the carbon monoxide pressure at 15 kg/cm$^2$. After feeding of the diisobutylene mixture was discontinued, stirring was continued for further 1 hour. An acid strength of the catalyst varied from $-8.1$ to $-7.5$ before and after this reaction.

After completion of the reaction, the resulting reaction mixture was diluted to three times with water and repeatedly extracted three times with 200 ml of n-hexane. Removal of n-hexane by distillation yielded 47.1 g of a crude carboxylic acid mixture having the composition as shown in Table 1 below.

This crude carboxylic acid mixture was distilled under reduced pressure to give 28.0 g of a fraction at $85°-101°$ C./mmHg.

Gas chromatography of this fraction revealed that it was a carboxylic acid mixture containing 31% by weight of a mixture composed of 2,2,4,4-tetramethylpentanoic acid and other carboxylic acids (referred to as "carboxylic acid (A)") and 69% by weight of a mixture composed of 2-ethyl-2,3,3-trimethylbutanoic acid, 2-isopropyl-2,3-dimethylbutanoic acid, 2,2,3,3-tetramethylpentanoic acid, 2,2,3,4-tetramethylpentanoic acid and other tertiary carboxylic acids (referred to as "carboxylic acid (B)").

The analytical conditions were the same as those given in definition of difficulty in esterification hereinabove.

Then, 50 g of this carboxylic acid mixture, 200 g of methanol and 2.7 g of zinc acetate were charged in a one-liter autoclave, followed by purging with nitrogen. The reaction was then carried out at 200° C. over a period of 5 hours. The reaction product was analyzed by gas chromatography to find that 15% of the carboxylic acid (A) was esterified and 80% of the carboxylic acid (B) was esterified. Therefore, according to the definition of difficulty in esterification, the carboxylic acid obtained in this example was a carboxylic acid mixture containing at least 55% of isomers of tertiary carboxylic acids which were difficult to esterify.

EXAMPLE 2

The procedures of Example 1 were followed in the same manner with the exception that 52.4 g of a polyolefin composed of 0.8% by weight of C11-olefin, 94.3% by weight of C12-olefin and 4.9% by weight of C13-olefin was used in place of 33.6 g of the diisobutylene mixture, yielding a crude carboxylic acid mixture having the composition as shown in Table 1 below. An acid strength of the catalyst reduced gradually during the reaction and varied from $-8.1$ to $-7.6$ before and after the reaction.

This crude carboxylic acid mixture was subjected to distillation under reduced pressure to give 46.6 g of a fraction at 119°–127° C.

This fraction was analyzed by gas chromatography to find that it was a carboxylic acid mixture (referred to as "carboxylic acid (B')") composed of 2,2,4,4,6,6-hexamethylbutanoic acid, 2-ethyl-2,3,3,5,5-pentamethylhexanoic acid, 2,4,4-trimethyl-2-t-pentylpentanoic acid, 2-isopentyl-2,4,4-trimethylpentanoic acid, 2-isopropyl-2,3,5,5-tetramethylhexanoic acid and other tertiary carboxylic acids.

Analytical conditions for gas chromatography were the same as for definition of difficulty in esterification given hereinabove.

The esterification was then carried out in substantially the same manner as in Example 1 except that the carboxylic acid (B') was used as a carboxylic acid mixture. The reaction product was analyzed by gas chromatography to find that 24% of the carboxylic acid (B') was esterified.

Therefore, according to the definition of difficulty in esterification given hereinabove, this carboxylic acid (B') obtained in this Example 2 was a carboxylic acid mixture containing at least 55% by weight of an isomer mixture of tertiary carboxylic acids difficult to esterify.

COMPARATIVE EXAMPLE 1

Esterification reaction was carried out in the same manner as in Example 1 except that pivalic acid (Shell Chemical Co.) was used.

Analysis of the reaction product by gas chromatography has revealed that 94% of pivalic acid was converted to methyl pivalate. The conditions for gas chromatography were substantially the same as given in definition of difficulty in esterification hereinabove except that a column was heated at 55° C. for 5 minutes and then the temperature was elevated to 250° C.

EXAMPLE 3

150 ml of a catalyst comprising an aqueous solution containing 85% by weight of sulfuric acid was charged in a reaction vessel, which was fully purged with carbon monoxide, followed by absorption of carbon monoxide to saturation.

To this reaction vessel was fed 0.3 mol of diisobutylene while keeping a reaction temperature at 25° C. and a reaction pressure at 5 kg/cm$^2$, thereby reacting diisobutylene with carbon monoxide. Carbon monoxide consumed by the reaction was replenished so as to maintain the given pressure.

After lapse of the reaction time of 1.5 hour, feeding of diisobutylene was discontinued and stirring was effected for further 1 hour. Thereafter, an equal amount of water was added.

The resulting reaction mixture was then diluted to three times with water and extracted repeatedly three times with 200 ml of n-hexane.

Removal of n-hexane by distillation yielded a carboxylic acid mixture having the composition as shown in Table 1 below. The composition of the reaction product was measured by NMR spectrum. The reaction conditions and results are also shown in Table 1 below.

EXAMPLES 4 AND 5

The procedures were followed in the same manner as in Example 3 with the exception that the reaction was carried out under the reaction pressure shown in Table 1 below. Results are also shown in Table 1 below.

EXAMPLE 6

The procedures of Example 3 were followed in the same manner with the exception that a catalyst comprising an aqueous solution containing 66% by weight of sulfuric acid and 22% by weight of boron trifluoride was used in place of the aqueous solution catalyst containing 85% by weight of sulfuric acid.

Results are shown in Table 1 below.

EXAMPLES 7 AND 8

The procedures of Example 3 were followed in the same manner with the exception that a reaction pressure as shown in Table 1 below was employed.

Results are shown in Table 1 below.

EXAMPLE 9

The procedures of Example 1 were followed in the same manner except that 10.4 g of silver oxide was used in place of 6.4 g of cuprous oxide.

Results are shown in Table 1 below.

COMPARATIVE EXAMPLES 2 AND 3

The procedures of Example 3 were followed in the same manner with the exception that a reaction pressure as shown in Table 1 below was employed.

Results are shown in Table 1 below. As will be apparent from the results shown in Table 1 below, it has been found in each of the comparative examples that 2,2,4,4-tetramethylpentanoic acid which is insufficient in a hydrolysis resistance, when esterified, was produced in larger amounts than in Example 3.

COMPARATIVE EXAMPLES 4 AND 5

The procedures of Example 6 were followed in the same manner with the exception that a reaction pressure as shown in Table 1 below was employed.

Results are shown in Table 1 below. As will be apparent from the results shown in Table 1 below, it has been found that 2,2,4,4-tetramethylpentanoic acid which is insufficient in a hydrolysis resistance, when esterified, was produced in larger amounts than in Example 6.

REFERENCE EXAMPLE 1

A one-liter stainless steel autoclave was charged with 200 ml of methanol and 50.0 g of a carboxylic acid mixture synthesized in the same manner as in Comparative Example 5 using a catalyst (acid strength: −8.1 to −7.5) comprising an aqueous solution composed of sulfuric acid and phosphoric acid, the carboxylic acid containing 2,2,4,4-tetramethylpentanoic acid (referred to as "carboxylic acid (A)" in the following description and in Table 1 below) and a mixture (referred to as "carboxylic acid (B)" in the following description and in Table 1 below) composed of 2-ethyl-2,3,3-trimethylbutanoic acid, 2-isopropyl-2,3-dimethylbutanoic acid, 2,2,3,4-tetramethylpentanoic acid, 2,2,3,4-tetramethylpentanoic acid and other tertiary carboxylic acids, in a ratio in mol of the carboxylic acid (A) to the carboxylic acid (B) of 53 to 47. The esterification reaction was then carried out at 225° C. for 12 hours.

The resulting reaction product was analyzed by gas chromatography that its conversion rate to methyl ester was 56%. Gas chromatography of the unreacted acids revealed that the molar ratio of the carboxylic acid (A) to the carboxylic acid (B) was as low as 17 to 83. From the above analytical results and the definition of easiness in esterification, it was clarified that the carboxylic acid (B) was markedly lower in esterification reactivity than the carboxylic acid (A).

REFERENCE EXAMPLE 2:

A 100-ml three necked flask was charged with 50 ml of hexamethylphosphoric triamide and 6.7 g of a carboxylic acid mixture (in the molar ratio of the carboxylic acid (A) to the carboxylic acid (B) of 53 to 47) synthesized in the same manner as in Comparative Example 5 using a catalyst (acid strength: −8.1 to −7.5) comprising an aqueous mixed solution of sulfuric acid and phosphoric acid. To this flask was added a 25% aqueous solution containing 2.43 g of sodium hydroxide and the mixture was stirred at room temperature for 30 minutes. To this mixture was added 10 g of methyl iodide, turning the solution immediately cloudy and precipitating sodium iodide.

The reaction mixture was poured in 50 ml of water and extracted with ether. The extraction solution was washed with water and then distilled to yield 7.2 g of methyl ester of carboxylic acids containing the esters of the carboxylic acid (A) and the esters of the carboxylic acid (B) in the molar ratio of the former to the latter of 53 to 47.

In a 500-ml flask were placed 1.2 ml of the methyl ester mixture and 400 ml of 0.1 N NaOH solution (water: ethylene glycol monomethyl ether=1:10) was added. The mixture was then left to stand in a thermostatic chamber of 80° C. for 50 hours to carry out alkali hydrolysis.

Gas chromatography of the reaction mixture revealed that the molar ratio of the carboxylic acid (A) to the carboxylic acid (B) changed to 27 to 78.

From the result and the definition of hydrolysis resistance given hereinabove, it was apparent that the ester of carboxylic acid (A) was more susceptible to hydrolysis than the ester of carboxylic acid (B).

EXAMPLES 10–15 AND COMPARATIVE EXAMPLES 6–10

A reaction vessel was charged with a catalyst comprising an aqueous solution of sulfuric acid and phosphoric acid (provided that no phosphoric acid was used in the Comparative Examples) and cuprous oxide in concentrations and amounts as shown in Table 2 below. After sufficiently purging the inside of the reaction vessel with carbon monoxide, the mixture was stirred to absorb carbon monoxide to saturation. Carbon monoxide was then reacted with diisobutylene under reaction conditions as shown in Table 2 while keeping the carbon monoxide pressure in the reaction vessel at 15 kg/cm$^2$. The carbon monoxide consumed during the reaction was replenished so as to compensate for its amount decreased. After the reaction was continued for 1.5 hours, a supply of the diisobutylene was discontinued and the mixture was stirred for another 1 hour. Then an equal amount of water was added.

The resulting reaction mixture was then extracted three times with 200 ml of n-hexane.

Some sulfuric acid contaminated in the extracts solution was removed by washing with water and n-hexane was distilled off, yielding a carboxylic acid mixture having the composition as shown in Table 2 below. The results are also shown in Table 2 below.

Content of sulfur in the resulting carboxylic acid mixtures was measured by trace sulfur analyzer (manufactured by Mitsubishi Chemical Co.) and cotent of phosphorus was determined by incinerating the carboxylic acid mixtures in an electric furnace, collecting the incinerated product, adding an indicator thereto and measuring absorbance for coloration.

TABLE 1

| | Units | Example 1 | 2 | 3 | 4 | 5 | 6 | 7 | 8 | 9 |
|---|---|---|---|---|---|---|---|---|---|---|
| Starting material | | | | | | | | | | |
| Kind of olefin*1 | | DIB | C$_{12}$PO | DIB | DIB | DIB | DIB | DIB | DIB | DIB |
| Amount of olefin used | g | 33.6 | 52.4 | 33.6 | 33.6 | 33.6 | 33.6 | 33.6 | 33.6 | 33.6 |
| Amount of carbon oxide used | mol | Replenished from gaseous phase for that consumed for the reaction | | | | | | | | |
| Feeding Time | min. | 90 | 90 | 90 | 90 | 90 | 90 | 90 | 90 | 90 |
| Catalyst | | | | | | | | | | |
| Concentration of sulfuric acid | wt % | 64 | 64 | 85 | 85 | 85 | 64 | 64 | 64 | 64 |
| Concentration of phosphoric acid | wt % | 29 | 29 | 0 | 0 | 0 | 29 | 29 | 29 | 29 |
| Water | wt % | 7 | 7 | 15 | 15 | 15 | 7 | 7 | 7 | 7 |
| Cu$_2$O | g | 6.4 | 6.4 | 0 | 0 | 0 | 0 | 0 | 0 | Ag$_2$O 10.4 |
| Amount of catalyst used | g | 270 | 270 | 270 | 270 | 270 | 270 | 270 | 270 | 270 |

TABLE 1-continued

| | | | | | | | | | | |
|---|---|---|---|---|---|---|---|---|---|---|
| Acid strength (acidity function $H_o$) | *2 | $-8.1 \sim -7.5$ | $-8.1 \sim -7.6$ | $-8.3 \sim -7.4$ | $-8.3 \sim -7.4$ | $-8.3 \sim -7.4$ | $-8.1 \sim -7.5$ | $-8.1 \sim -7.5$ | $-8.1 \sim -7.4$ | $-8.1 \sim -7.5$ |
| Reaction temperature | °C. | 25 | 5 | 25 | 25 | 25 | 25 | 25 | 25 | 25 |
| Reaction pressure | kg/cm² G | 15 | 15 | 5 | 10 | 15 | 5 | 10 | 15 | 15 |
| Amount of sulfer in product | wt ppm | — | — | — | — | — | — | — | — | — |
| Composition of acid products | | | | | | | | | | |
| Hydrocarbon oil | wt % | 0.5 | 1.1 | 37.7 | 1.6 | 0.1 | — | — | — | — |
| Trimethyl acetic acid | wt % | 8.2 | 7.6 | 7.6 | 6.2 | 9.0 | — | — | — | — |
| $C_6$ acid | wt % | 1.9 | 2.5 | 4.9 | 3.1 | 2.9 | — | — | — | — |
| $C_{7,8}$ acid | wt % | 2.6 | 3.2 | 5.7 | 4.1 | 4.0 | — | — | — | — |
| $C_9$ acid | wt % | 59.4 | 17.8 | 21.8 | 34.6 | 53.8 | — | — | — | — |
| $C_{10-13}$ acid | wt % | 26.8 | 66.5 | 22.3 | 50.4 | 30.2 | — | — | — | — |
| $C_{14+}$ acid | wt % | 0.6 | 1.3 | | | | — | — | — | — |
| Composition of $C_6$ Carboxylic acid | | | | | | | | | | |
| Carboxylic acid (A) | wt % | 31 | — | 16 | 22 | 26 | 17 | 23 | 25 | 24 |
| Carboxylic acid (B) | wt % | 69 | — | 84 | 78 | 74 | 83 | 77 | 75 | 75 |
| Composition of $C_{13}$ Carboxylic acid | | | | | | | | | | |
| Carboxylic acid (A) | wt % | 31 | 0 | — | — | — | — | — | — | — |
| Carboxylic acid (B) | wt % | 69 | 100 | — | — | — | — | — | — | — |

| | | Comparative Example | | | | |
|---|---|---|---|---|---|---|
| | Units | 1 | 2 | 3 | 4 | 5 |
| Starting material | | | | | | |
| Kind of olefin*1 | | — | DIB | DIB | DIB | DIB |
| Amount of olefin used | g | — | 33.6 | 33.6 | 33.6 | 33.6 |
| Amount of carbon oxide used | mol | — | Replenished from gaseous phase for that consumed for the reaction | | | |
| Feeding Time | min. | — | 90 | 90 | 90 | 90 |
| Catalyst | | | | | | |
| Concentration of sulfuric acid | wt % | — | 85 | 85 | 64 | 64 |
| Concentration of phosphoric acid | wt % | — | 0 | 0 | 29 | 29 |
| Water | wt % | — | 15 | 15 | 7 | 7 |
| $Cu_2O$ | g | — | 0 | 0 | 0 | 0 |
| Amount of catalyst used | g | — | 270 | 270 | 270 | 270 |
| Acid strength (acidity function $H_o$) | *2 | — | $-8.3 \sim -7.4$ | $-8.3 \sim -7.4$ | $-8.1 \sim -7.5$ | $-8.1 \sim -7.5$ |
| Reaction temperature | °C. | — | 25 | 25 | 25 | 25 |
| Reaction pressure | kg/cm² G | — | 50 | 70 | 50 | 70 |
| Amount of sulfer in product | wt ppm | — | — | — | — | — |
| Composition of acid products | | | | | | |
| Hydrocarbon oil | wt % | — | 0.0 | — | — | — |
| Trimethyl acetic acid | wt % | 100 | 11.1 | — | — | — |
| $C_6$ acid | wt % | — | 0.5 | — | — | — |
| $C_{7,8}$ acid | wt % | — | 0.7 | — | — | — |
| $C_9$ acid | wt % | — | 74.5 | — | — | — |
| $C_{10-13}$ acid | wt % | — | — | — | — | — |
| $C_{14+}$ acid | wt % | — | 13.2 | — | — | — |
| Composition of $C_6$ Carboxylic acid | | | | | | |
| Carboxylic acid (A) | wt % | — | 48 | 52 | 49 | 53 |
| Carboxylic acid (B) | wt % | — | 52 | 48 | 51 | 47 |
| Composition of $C_{13}$ Carboxylic acid | | | | | | |
| Carboxylic acid (A) | wt % | — | — | — | — | — |
| Carboxylic acid (B) | wt % | — | — | — | — | — |

*1: DIB . . . diisobutylen. $C_{12}PO$: $C_{12}$ polyolefin.
*2: Acid strength . . . Hammett's acidity function $H_o$. (Initial value in reaction)~(End value in reaction)
*3: $C_6$ acid represents $C_6$ carboxylic acid, $C_{7,8}$ acid represents $C_7$ or $C_8$ carboxylic acid, $C_9$ acid represents $C_9$ carboxylic acid, $C_{10-13}$ acid represents $C_{10}\sim C_{13}$ carboxylic acid and $C_{14+}$ acid represents $C_{14}$ carboxylic acid.

TABLE 2

| | | Example | | Comp. Example | | Example | | | | Comparative Example | | |
|---|---|---|---|---|---|---|---|---|---|---|---|---|
| | Units | 10 | 11 | 6 | 7 | 12 | 13 | 14 | 15 | 8 | 9 | 10 |
| Starting material | | | | | | | | | | | | |
| Kind of olefin*1 | | DIB | DIB | DIB | DIB | $C_{12}PO$ | $C_{12}PO$ | $C_{12}PO$ | $C_{12}PO$ | $C_{12}PO$ | $C_{12}PO$ | $C_{12}PO$ |
| Amount of olefin used | g | 0.3 | 0.3 | 0.3 | 0.3 | 0.3 | 0.3 | 0.3 | 0.3 | 0.3 | 0.3 | 0.3 |
| Amount of carbon oxide used | mol | 0.3 | 0.3 | 0.3 | 0.3 | 0.3 | 0.3 | 0.3 | 0.3 | 0.3 | 0.3 | 0.3 |
| Feeding Time | min. | 90 | 90 | 90 | 90 | 90 | 90 | 90 | 90 | 90 | 90 | 90 |
| Catalyst | | | | | | | | | | | | |
| Concentration of sulfuric acid | wt % | 64 | 52 | 87 | 90 | 64 | 64 | 64 | 64 | 80 | 60 | 40 |
| Concentration of phosphoric acid | wt % | 29 | 45 | 0 | 0 | 29 | 29 | 29 | 29 | 15 | 35 | 55 |
| Water | wt % | 7 | 3 | 13 | 10 | 7 | 7 | 7 | 7 | 5 | 5 | 5 |
| $Cu_2O$ | g | 6.4 | 6.4 | 6.4 | 6.4 | 6.4 | 6.4 | 6.4 | 6.4 | 0 | 0 | 0 |
| Amount of catalyst used | g | 150 | 150 | 150 | 150 | 150 | 150 | 150 | 150 | 150 | 150 | 150 |
| Acid strength (acidity function $H_o$) | *2 | $-8.1 \sim -7.5$ | $-8.2 \sim -7.5$ | $-8.1 \sim -7.4$ | $-8.1 \sim -7.5$ | $-8.1 \sim -7.4$ | $-8.1 \sim -7.5$ | $-8.1 \sim -7.5$ | $-8.2 \sim -7.5$ | $-8.2 \sim -7.5$ | $-8.2 \sim -7.8$ | $-8.2 \sim -7.8$ |
| Reaction temperature | °C. | 25 | 25 | 25 | 25 | 15 | 5 | 5 | 5 | 25 | 25 | 25 |
| Reaction pressure | kg/cm² G | 15 | 15 | 15 | 15 | 15 | 15 | 15 | 15 | 50 | 50 | 50 |

TABLE 2-continued

|  | Units | Example 10 | Example 11 | Comp. Example 6 | Comp. Example 7 | Example 12 | Example 13 | Example 14 | Example 15 | Comparative Example 8 | Comparative Example 9 | Comparative Example 10 |
|---|---|---|---|---|---|---|---|---|---|---|---|---|
| Amount of sulfer in product | wt ppm | 410 | 400 | 1770 | 2190 | 950 | 330 | 240 | 340 | 600 | 850 | 25 |
| Composition of acid products |  |  |  |  |  |  |  |  |  |  |  |  |
| Hydrocarbon oil | wt % | 0.5 | 2.6 | 5.4 | 0.8 | 0.4 | 1.1 | 2.3 | 0.0 | 0.8 | 0.1 | 72.0 |
| Trimethyl acetic acid | wt % | 8.3 | 10.2 | 10.4 | 14.0 | 10.5 | 7.5 | 1.5 | 4.7 | 22.8 | 20.7 | 3.6 |
| $C_6$ acid | wt % | 2.0 | 2.6 | 1.6 | 2.6 | 3.3 | 2.6 | 0.6 | 1.9 | 2.1 | 2.4 | 1.2 |
| $C_{7,8}$ acid | wt % | 2.8 | 3.2 | 1.8 | 3.3 | 3.9 | 3.2 | 0.4 | 1.2 | 2.6 | 3.0 | 1.1 |
| $C_9$ acid | wt % | 59.3 | 53.6 | 59.5 | 52.9 | 23.7 | 17.7 | 7.8 | 20.1 | 31.2 | 31.4 | 7.6 |
| $C_{10-13}$ acid | wt % | 27.1 | 27.8 | 21.3 | 23.4 | 57.0 | 67.5 | 87.4 | 70.1 | 40.0 | 42.0 | 14.4 |
| $C_{14+}$ acid | wt % |  |  |  |  | 1.2 | 0.3 |  |  | 0.1 | 0.4 | 0.1 |

*1: DIB ... diisobutylen. $C_{12}PO$: $C_{12}$ polyolefin.
*2: Acid strength ... Hammett's acidity function $H_o$. (Initial value in reaction)~(End value in reaction)
*3: $C_6$ acid represents $C_6$ carboxylic acid, $C_{7,8}$ acid represents $C_7$ or $C_8$ carboxylic acid, $C_9$ acid represents $C_9$ carboxylic acid, $C_{10-13}$ acid represents $C_{10}$~$C_{13}$ carboxylic acid and $C_{14+}$ acid represents $C_{14}$ carboxylic acid.

What is claimed is:

1. In a process for the production of carboxylic acids providing esters unlikely to be hydrolyzable, which comprises reacting a polyolefin with carbon monoxide and water in the presence of a catalyst comprising sulfuric acid, phosphoric acid and a metal oxide;

the improvement comprising reacting a polyolefin containing an isobutylene unit at a rate of 60% by weight or higher with carbon monoxide and water under reaction pressure ranging from 2 to 40 kg/cm² at reaction temperature ranging from −10° C. to 80° C. in the presence of a catalyst comprising sulfuric acid in an amount of sulfuric acid in the catalyst of at least 3 moles with respect to one mole of C=C double bonds in the polyolefin and in amounts of carbon monoxide and water of at least one mole equivalent to the C=C double bonds in the polyolefin, said catalyst being selected from the group consisting of a catalyst comprising an aqueous sulfuric acid solution in concentrations of 73% to 98% by weight, and a catalyst comprising an aqueous sulfuric acid solution in concentrations of 73% to 98% by weight, and phosphoric acid, each having an acid strength within a range from −6 to −9.2 or said catalyst comprising an aqueous sulfuric acid solution in concentrations of 73% to 98% by weight, phosphoric acid in concentrations of 70% by weight or less with respect to the combined quantity of the sulfuric acid aqueous solution and phosphoric acid, and a metal oxide in concentrations of 0.1% to 4% by weight with respect to the combined quantity of the sulfuric acid aqueous solution and phosphoric acid.

2. A process as claimed in claim 1, wherein said metal oxide is cuprous oxide or silver oxide.

3. A process as claimed in claim 1, wherein said polyolefin is a reaction product obtainable by polymerizing a butane-butylene fraction obtained by cracking of naphtha in the presence of an acid catalyst.

4. A process for producing a mixture of tertiary carboxylic acids comprising:

reacting an olefin selected from the group consisting of diisobutylene and triisobutylene with carbon monoxide and water in the presence of a catalyst consisting of sulfuric acid and phosphoric acid under a pressure of 2–40 kg/cm², wherein the concentration of said sulfuric acid in the catalyst is 30–90% by weight and the concentration of said phosphoric acid in the catalyst is 5–70% by weight.

5. The process according to claim 4 wherein said catalyst additionally contains a metal compound.

6. The process according to claim 5 wherein said metal compound is a metal oxide.

7. The process according to claim 6 wherein said metal oxide is cuprous oxide.

8. The process according to claim 5 wherein the content of said metal compound is 0.2–1% by weight of the mixture of sulfuric acid and phosphoric acid.

9. A mixture of tertiary carboxylic acids formed according to the process of claim 4;

wherein said mixture contains at least 55% by weight of an isomeric mixture of tertiary carboxylic acids selected from the group consisting of isomeric mixtures of tertiary carboxylic acids having 9 carbon atoms and isomeric mixtures of tertiary carboxylic acids having 13 carbon atoms, said carboxylic acids being difficult to esterify as defined by the fact that the reaction product obtained by reacting said tertiary carboxylic acids with methanol in an amount four times the weight of the carboxylic acids in the presence of zinc acetate as a catalyst in an amount of 5.4% by weight of the carboxylic acids at a reaction temperature of 200° C. and a reaction time of five hours has, according to gas chromatography, a conversion rate of the starting tertiary carboxylic acids to the carboxylic acid esters of 40% or less.

10. A mixture containing at least 55% of weight of a mixture of isomers of tertiary carboxylic acids which are difficult to esterify with methanol when said tertiary carboxylic acids are reacted with an amount of methanol which is four times the weight of the tertiary carboxylic acids, said esterification being effected in the presence of 5.4%, by weight of the carboxylic acids, of a zinc acetate catalyst, said esterification being conducted under esterification conditions at a reaction temperature of 200° C. and a reaction time of five hours, said tertiary carboxylic acids being prepared from a polyolefin containing at least 60% of isobutylene units.

* * * * *